US012687534B2

(12) United States Patent
Kornbluth et al.

(10) Patent No.: US 12,687,534 B2
(45) Date of Patent: Jul. 21, 2026

(54) SOIL SAMPLERS FOR MONITORING SOIL CONDITIONS

(71) Applicant: Robert Bosch GmbH, Stuttgart (DE)

(72) Inventors: Mordechai Kornbluth, Brighton, MA (US); Karim Gadelrab, Boston, MA (US); Soo Kim, Arlington, MA (US); Jonathan Mailoa, Cambridge, MA (US); Georgy Samsonidze, San Francisco, CA (US); Kaushal Sagar, Singapore (SG)

(73) Assignee: Robert Bosch GmbH (DE)

( * ) Notice: Subject to any disclaimer, the term of this patent is extended or adjusted under 35 U.S.C. 154(b) by 416 days.

(21) Appl. No.: 17/480,656

(22) Filed: Sep. 21, 2021

(65) Prior Publication Data

US 2023/0088971 A1     Mar. 23, 2023

(51) Int. Cl.
| | |
|---|---|
| *G01N 33/24* | (2006.01) |
| *G01N 1/04* | (2006.01) |
| *G01N 21/64* | (2006.01) |
| *G01N 21/78* | (2006.01) |
| *G01N 27/333* | (2006.01) |

(52) U.S. Cl.
CPC ............... *G01N 33/24* (2013.01); *G01N 1/04* (2013.01); *G01N 21/643* (2013.01); *G01N 21/78* (2013.01); *G01N 27/333* (2013.01); *G01N 2021/6439* (2013.01); *G01N 33/245* (2024.05)

(58) Field of Classification Search
CPC ........ G01N 33/24; G01N 1/04; G01N 21/643; G01N 21/78; G01N 27/333
See application file for complete search history.

(56) References Cited

U.S. PATENT DOCUMENTS

| | | | | |
|---|---|---|---|---|
| 4,013,413 A | * | 3/1977 | Stewart .................. | G01N 35/08 |
| | | | | 436/52 |
| 7,186,567 B1 | * | 3/2007 | Sutherland ....... | G01N 33/54366 |
| | | | | 252/582 |

(Continued)

FOREIGN PATENT DOCUMENTS

| | | |
|---|---|---|
| CN | 112014339 A | 12/2020 |
| WO | 8000273 A1 | 2/1980 |

OTHER PUBLICATIONS

Carter et al. "Fluorescent Sensors for Measuring Metal Ions in Living Systems", Chem. Rev. 2014, vol. 114, pp. 4564-4601.

(Continued)

*Primary Examiner* — Lyle Alexander
*Assistant Examiner* — Dwan A Gerido
(74) *Attorney, Agent, or Firm* — Dickinson Wright PLLC

(57)     ABSTRACT

A soil sampler attachable to a vehicle for agricultural uses includes a collector configured to collect a soil sample from a field as the vehicle advances across the field. The soil sampler further includes a preprocessor connected to the collector and configured to receive the soil sample from the collector and to preprocess the soil sample to dilute the soil sample. The soil sampler also includes a sensor connected to the preprocessor and configured to determine a concentration of at least one analyte in the soil sample. The soil sampler further includes a disposer connected to the sensor and configured to dispose the soil sample after the sensor determines the concentration of the at least one analyte in the soil sample.

19 Claims, 8 Drawing Sheets

(56) References Cited

U.S. PATENT DOCUMENTS

| | | | |
|---|---|---|---|
| 2004/0048241 A1 | 3/2004 | Freeman et al. | |
| 2005/0172733 A1* | 8/2005 | Drummond | A01B 79/005 |
| | | | 73/864.41 |
| 2010/0283993 A1* | 11/2010 | Preiner | G01N 21/276 |
| | | | 356/442 |
| 2012/0103077 A1* | 5/2012 | Koshnick | G01N 33/24 |
| | | | 73/64.56 |
| 2017/0254766 A1* | 9/2017 | Bermudez Rodriguez | |
| | | | G01N 27/301 |
| 2018/0224419 A1* | 8/2018 | Gerber-Siff | G01N 1/4077 |
| 2020/0393382 A1* | 12/2020 | van den Haak | A01C 21/002 |
| 2020/0396893 A1 | 12/2020 | Koch et al. | |
| 2021/0025790 A1* | 1/2021 | Fiechter | G01N 1/08 |
| 2021/0190695 A1* | 6/2021 | Kornbluth | C07D 515/14 |
| 2022/0064029 A1* | 3/2022 | Suss | C02F 1/4691 |
| 2022/0364998 A1* | 11/2022 | Koch | G01N 21/78 |

OTHER PUBLICATIONS

Rosenberg et al. "In-field determination of soil ion content using a handheld device and screen-printed solid-state ion-selective electrodes", PloS ONE 2018, vol. 13, No. 9, 20 Pages.
Dimeski et al. "Ion Selective Electrodes (ISEs) and interferences—A review", Clinica Chimica Acta 2010, vol. 411, pp. 309-317.
Shrivastava et al. "Linking capacity loss and retention of nickel hexacyanoferrate to a two-site intercalation mechanism for aqueous $Mg^{2+}$ and $Ca^{2+}$ ions†", Phys.Chem.Chem.Phys. 2019, vol. 21, pp. 20177-20188.
Written Opinion and International Search Report for PCT/US2022/44261 Dated, Jan. 5, 2023, All together 12 Pages.

* cited by examiner

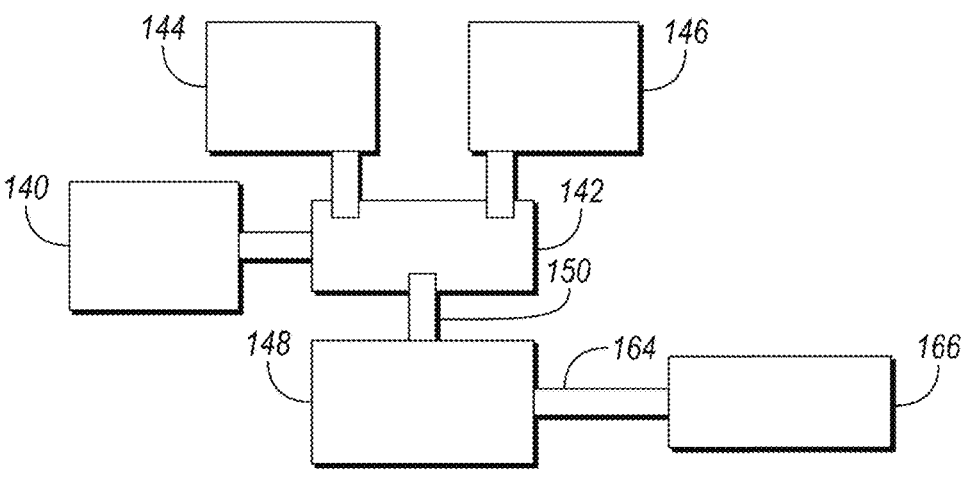
FIG. 5A
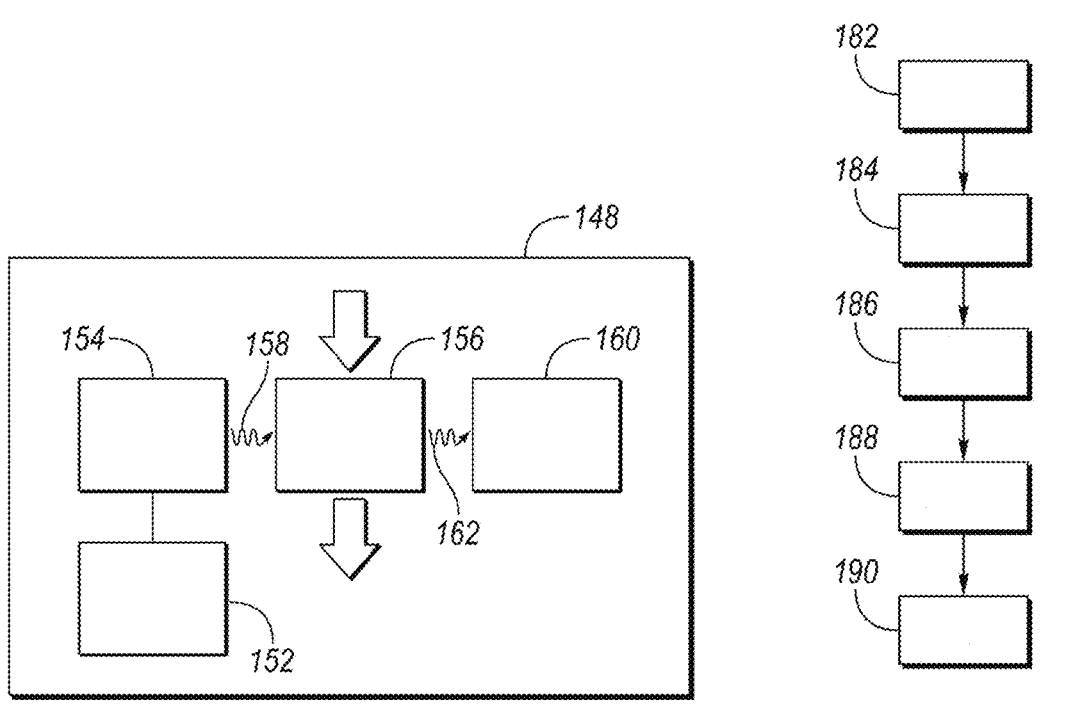
FIG. 5B
FIG. 5C

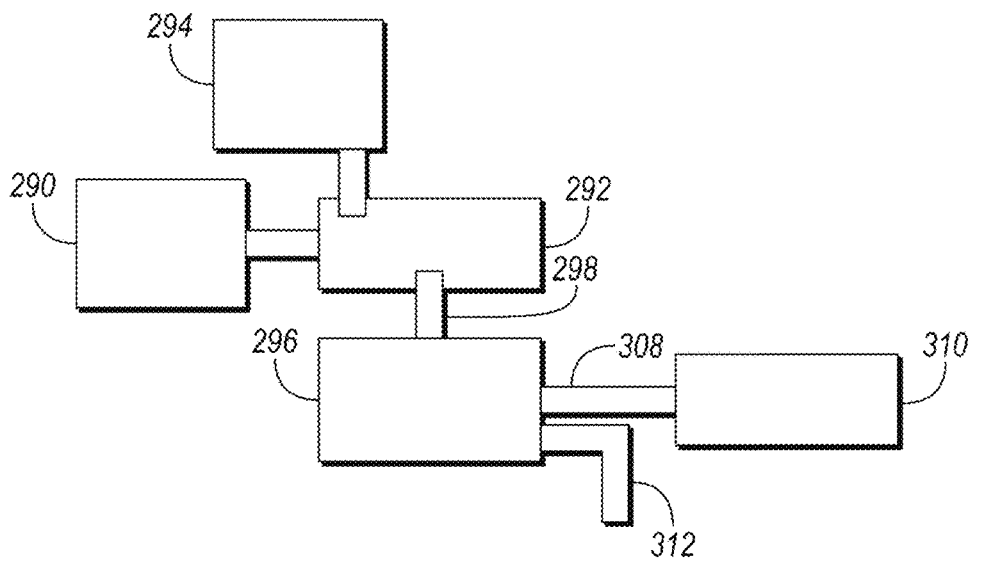
FIG. 7A
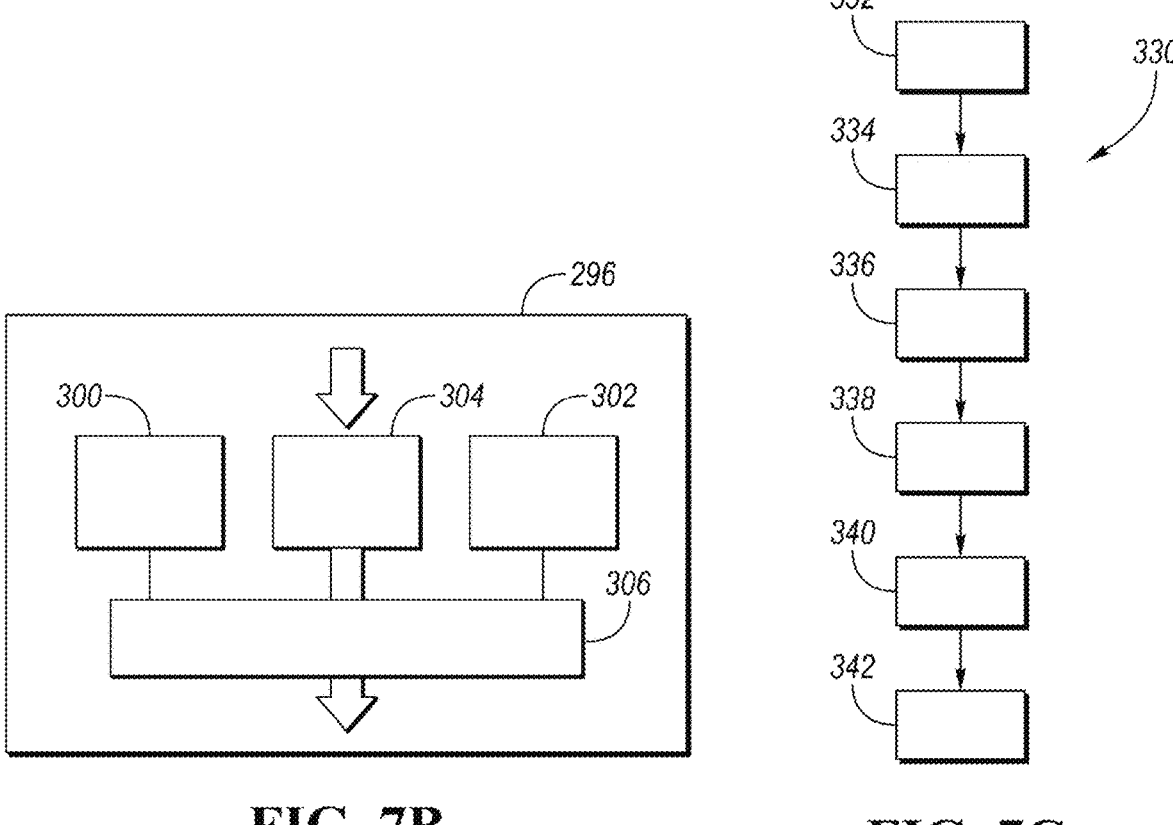
FIG. 7B
FIG. 7C

SOIL SAMPLERS FOR MONITORING SOIL CONDITIONS

TECHNICAL FIELD

The present disclosure relates to soil samplers for monitoring soil conditions, more specifically, a soil sampler attachable to a vehicle for monitoring soil conditions in a field (e.g. a ground or soil) as the vehicle advances across the field.

BACKGROUND

Food is one of the most important resources for living beings, which plays an essential role in health promotion, disease prevention and population growth. A view that is sometimes referred to as a Malthusian catastrophe observes that population growth is potentially exponential while the growth of the food supply or other resources is roughly linear. When population growth outpaces food production, poverty and depopulation may occur. Significant political and economic forces have thus been invested in securing efficient food supplies. For example, in order to obtain healthy and nourishing soil, farmers take sabbatical fallows, implement crop rotations and use fertilizers to a field (e.g. a ground or soil).

SUMMARY

According to one embodiment, a soil sampler attachable to a vehicle for agricultural uses is disclosed. The soil sampler may include a collector configured to collect a soil sample from a field as the vehicle advances across the field. The soil sample may further include a preprocessor connected to the collector and configured to receive the soil sample from the collector and to preprocess the soil sample to dilute the soil sample. The soil sampler may also include a sensor connected to the preprocessor and configured to determine a concentration of at least one analyte in the soil sample. The soil sampler may further include a disposer connected to the sensor and configured to dispose the soil sample after the sensor determines the concentration of the at least one analyte in the soil sample.

According to another embodiment, a soil sampler attachable to a vehicle for agricultural uses is disclosed. The soil sampler may include a collector configured to collect a soil sample from a field as the vehicle advances across the field. The soil sample may further include a sensor connected to the collector. The sensor may include a power source. The sensor may further include a heat source powered by the power source and configured to emit heat to the soil sample to vaporize the soil sample, thereby generating light with an optical frequency. The sensor may also include an optical spectrum sensor configured to measure the optical frequency and to calculate a concentration of at least one analyte in the soil sample based on the optical frequency. The soil sample may further include a disposer connected to the sensor and configured to dispose the soil sample after the sensor calculates the concentration of the at least one analyte in the soil sample.

According to yet another embodiment, a method of determining soil conditions of a field when a vehicle for agricultural uses advances across the field is disclosed. The method may include collecting soil samples from the field. The method may further include preprocessing the soil samples. The method may also include sensing at least one analyte in the soil samples after preprocessing the soil samples. The method may further include calculating a concentration of the at least one analyte in the soil samples after sensing the soil sample. The method may also include disposing the soil samples.

BRIEF DESCRIPTION OF THE DRAWINGS

FIG. 5A depicts a schematic diagram of the soil sampler described in FIG. 2 according to a second embodiment of the present disclosure.

FIG. 5B depicts a schematic diagram of the sensor in FIG. 5A.

FIG. 5C depicts a flow chart illustrating a method of detecting soil conditions of the soil in a field (e.g. a ground or soil) using the soil sampler described in FIG. 5A.

FIG. 7A depicts a schematic diagram of the soil sampler described in FIG. 2 according to a fifth embodiment of the present disclosure.

FIG. 7B depicts a schematic diagram of the sensor in FIG. 7A.

FIG. 7C depicts a flow chart illustrating a method of detecting soil conditions of the soil in a field (e.g. a ground or soil) using the soil sampler described in FIG. 7A.

DETAILED DESCRIPTION

Figure 1:
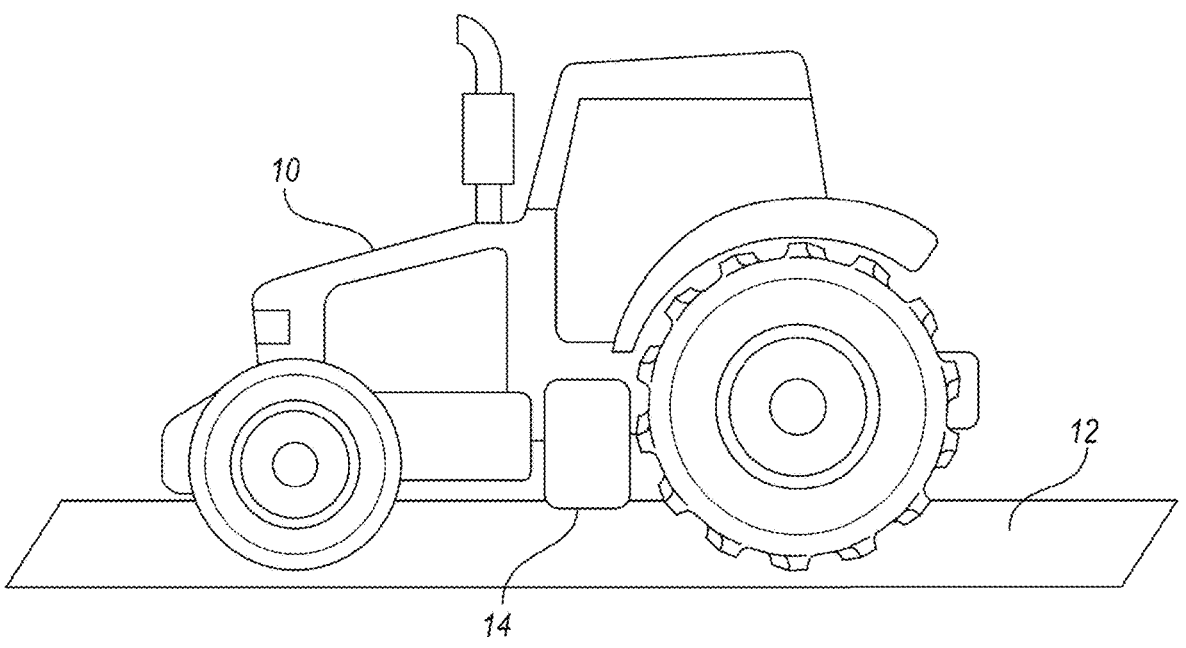
FIG. 1 depicts a representative side view of a vehicle for agricultural uses according to the present disclosure.

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Maintaining healthy soil conditions, such as sufficient soil nutrient contents, is critical in food production. Soil testing offers a convenient way to monitor the soil conditions. A typical soil testing may determine at least one analyte in the soil. The at least one analyte may be ions. Some of the analytes may include nitrogen (N), phosphorus (P), potassium (K), calcium (Ca), magnesium (Mg), sulfur(S), aluminum (Al), mercury (Ag), and lead (Pb). Among these analytes, N, P and K are the most important nutrients, often referred to as "NPK" nutrients in fertilizers. To conduct a soil testing, soil samples are often randomly selected from a field. For example, a farmer may randomly collect soil samples in a field and send the soil samples to a laboratory for soil testing. Upon receiving a testing result, the farmer may, however, arbitrarily evaluate soil conditions of the entire field based on these randomly selected soil samples. Admittedly, these soil samples may not accurately represent the soil conditions of the entire field. Therefore, when the farmer applies fertilizers to the field based on the testing result, some regions of the field may be over-fertilized, and some may be under fertilized, resulting in economic and ecological wastes. Therefore, there is a need for a solution to monitor the soil conditions in a field (e.g. a ground or soil) in a cost-efficient manner.

Aspects of the present disclosure relate to soil samplers for monitoring soil conditions, more specifically, a soil sampler attachable to a vehicle for monitoring soil conditions in a field (e.g. a ground or soil) as the vehicle advances across the field. In one embodiments, a soil sample may include a collector configured to collect a soil sample from a field as the vehicle advances across the field; a preprocessor connected to the collector and configured to receive the soil sample from the collector and to preprocess the soil sample to dilute the soil sample; a sensor connected to the preprocessor and configured to determine a concentration of at least one analyte in the soil sample; and a disposer connected to the sensor and configured to dispose the soil sample after the sensor determines the concentration of the at least one analyte in the soil sample. In another embodiment, a soil sampler may include a collector configured to collect a soil sample from a field as the vehicle advances across the field; a sensor connected to the preprocessor and configured to determine a concentration of at least one analyte in the soil sample; and a disposer connected to the sensor and configured to dispose the soil sample after the sensor determines the concentration of the at least one analyte in the soil sample. In yet another embodiment, a method of determining soil conditions of a field when a vehicle for agricultural uses advances across the field may include collecting soil samples from the field; preprocessing the soil samples; sensing at least one analyte in the soil samples after preprocessing the soil samples; calculating a concentration of the at least one analyte in the soil samples after sensing the soil sample; and disposing the soil samples.

FIG. 1 depicts a representative side view of a vehicle for agricultural uses according to the present disclosure. The vehicle 10 may be capable of mechanizing agricultural tasks, such as propelling a field 12 (e.g. ground or soil) for the purpose of processing the field 12 or objects (e.g. plants or crops) lying on or in the field 12. In some embodiments, the vehicle 10 may be a tractor, a plough (or plow), a planter, an off-road vehicle, or the like. In some other embodiments, the vehicle 10 may be an autonomous vehicle (e.g. a drone), a remote-controlled vehicle, or the like.

As illustrated in FIG. 1, the vehicle 10 may include a soil sampler 14 disposed thereon. In some embodiments, the soil sampler 14 may be disposed on a bottom side of the vehicle 10 facing a surface of the field 12. The soil sampler 14 may be removably attached to the vehicle 10 or integrated with the vehicle 10. The soil sampler 14 may be operated in a working mode as the vehicle 10 advances across the field 12, during which the soil sampler 14 may collect soil samples from regions of the soil in the field 12 and determine the soil conditions (e.g. soil nutrient contents) of those regions of the field 12 in real time. The soil sampler 14 may determine the soil conditions by detecting at least one analyte in the soil samples, and may further calculate a concentration of the at least one analyte in the soil samples. The at least one analyte may be ions. The at least one analyte may be N-containing analytes, P-containing analytes, K-containing analytes, Ca-containing analytes, Mg-containing analytes, S-containing analytes, Al-containing analytes, Ag-containing analytes, Pb-containing analytes, or a combination thereof. The N-containing analytes may be nitrate ($NO_3^-$) or ammonium ($NH_4^+$) ions.

If the soil sampler 14 detects that some regions of the field 12 contain a relatively higher concentration of N-, P- and/or K-containing analytes, soil conditions in those regions may be determined to be healthy (e.g. with sufficient soil nutrient contents such as fertilizers). If, however, the soil sampler 14 detects that some regions of the field 12 contain a relatively lower concentration of N-, P- and/or K-containing analytes, soil conditions in those regions may be determined to be less healthy (e.g. without sufficient soil nutrients contents such as fertilizers). In response, farmers may take actions to improve the soil conditions in those regions, such as by applying fertilizers to the soil in those regions. Furthermore, if the soil sampler 14 senses contaminations, such as heavy metals (e.g. Ag or Pb), in some regions of the field 12, farmers may accordingly take remedial measures to remove the contaminations from the soil in those regions.

Figure 2A:
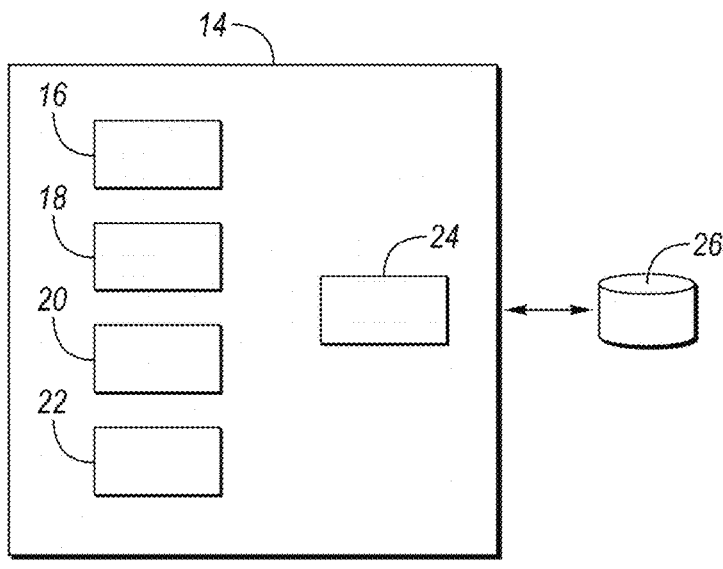
FIG. 2A depicts a schematic diagram of the soil sampler described in FIG. 1.

FIG. 2A depicts a schematic diagram of the soil sampler 14 described in FIG. 1. The soil sampler 14 may be disposed on a vehicle, for example, the vehicle 10 of FIG. 1. The soil sampler 14 may be disposed on a bottom side of the vehicle 10 facing a surface of the field 12 of FIG. 1. The soil sampler 14 may be removably attached to the vehicle 10 or integrated with the vehicle 10. The soil sampler 14 may be configured to determine the soil conditions of the soil in the field 12 as the vehicle 10 advances across the field 12. The soil sampler 14 may determine the soil conditions by detecting at least one analyte in the collected soil samples, and may further calculate a concentration of the at least one analyte in the soil samples. The at least one analyte may be ions. The at least one analyte may be N-containing analytes, P-containing analytes, K-containing analytes, Ca-containing analytes, Mg-containing analytes, S-containing analytes, Al-containing analytes, Ag-containing analytes, Pb-containing analytes, or a combination thereof. The N-containing analytes may be $NO_3^-$ or $NH_4^+$ ions.

As shown in FIG. 2A, the soil sampler 14 may include a collector 16 configured to collect soil samples from the field 12 as the vehicle 10 advances across the field 12. The collector 16 may be a soil probe, which, upon a force is applied thereto, may extend a depth into the field 12 to obtain a soil sample. In some embodiments, the soil sample may include a soil amount of 1 to 10 g.

The soil sampler 14 may further include a preprocessor 18 configured to preprocess the soil sample before the soil sampler senses the soil conditions of the soil sample. The preprocessor 18 may initially obtain a baseline measurement without the presence of the soil sample. In some embodiments, to preprocess the soil sample, the preprocessor 18 may dilute the soil sample with a liquid. The liquid may be water. The water may be deionized water, tap water, or water with known ion contents. A ratio of the soil amount in the soil sample to the liquid is at least 0.1. In some other embodiments, to preprocess the soil sample, the preprocessor 18 may further introduce a chemical reagent to the diluted soil sample. The chemical reagent may be a color reagent, such as sodium acetate. In yet some other embodiments, to preprocess the soil sample, the preprocessor 18 may centrifuge and/or filter the diluted soil sample to remove some particles in the soil sample. Examples of the particles may include rocks, oils, glass, plastics, or the like.

Referring to FIG. 2A, the soil sampler 14 may also include a sensor 20 configured to determine the soil conditions of the soil sample. Soil conditions may refer to soil nutrient contents (e.g. a concentration of at least one analyte) in the soil sample. In some embodiments, the sensor 20 may include at least one chemosensor configured to detect at least one analyte in the soil sample. The at least one chemosensor may capture (e.g. bind to) at least one analyte in the soil sample. The at least one chemosensor may be embedded in or attached to a sensor film of the sensor. Upon capturing the at least one analyte, the at least one chemosensor may generate a signal, such as fluorescence. The sensor may further include a detector configured to detect the signal and to calculate a concentration of the at least one analyte in the soil sample based on the signal. The detector may be a photodetector, such as a photodiode or a photoresistor.

In some other embodiments, the sensor 20 may include an optical detector with optical color filters configured to detect the presence of at least one analyte in the soil sample and to calculate a concentration of the at least one analyte in the soil sample by colorimetric analysis, i.e. by measuring a color intensity of the soil sample with the aid of a color reagent, such as sodium acetate. The optical detector may be a camera or a photodiode.

In yet some other embodiments, the sensor 20 may include a heat source configured to vaporize the soil sample, thereby generating light with an optical frequency (e.g. an absorption or emission spectrum). The sensor may further include an optical spectrum sensor configured to measure the optical frequency and to calculate a concentration of at least one analyte in the soil sample based on the optical frequency.

In still yet some other embodiments, the sensor 20 may include an electrode configured to detect at least one analyte in the soil sample. The electrode may be an ion-selective electrode (ISE) configured to bind to at least one analyte in the soil sample. Upon binding to the at least one analyte, a change of an electrical potential of the electrode may be detected and measured. The sensor may be configured to calculate a concentration of the at least one analyte in the soil sample based on the change of the electric potential. The electrode may also be an intercalation electrode configured to intercalate at least one analyte in the soil sample at certain potentials. Upon intercalating the at least one analyte, a change of open-circuit voltage of the electrode may be detected and measured. The sensor may be configured to calculate a concentration of the at least one analyte in the soil sample based on the change of the open-circuit voltage.

Referring to FIG. 2A, the soil sampler 20 may also include a disposer 22 configured to either dispose the soil sample back to the field 12 or to a waste reservoir of the soil sampler 14 after sensing. For example, if a color reagent is used in the sensor 20, disposing the soil sample back to the field 12 can be harmful to the field 12; instead, depositing the soil sample to the waste reservoir of the soil sampler 14 may help avoid ecological wastes in the field 12. In some embodiments, the disposer 22 may also include a cleaning cycle configured to rinse the soil sampler 14 with clean water after sensing.

In FIG. 2A, the soil sampler 14 may further include a tracker 24 configured to record a time and a location where the soil sample is collected from the field 12. The tracker 24 may be a global positioning system (GPS) tracker, a Bluetooth tracker, a near-field communication (NFC) tracker, a Wi-Fi tracker, or the like.

The soil sampler 14 of FIG. 2A may also include or operatively communicate with a data processor 26 configured to process data regarding the soil conditions of the soil samples collected from the field 12. The data may include, but not limited to, concentrations of at least one analyte in the soil samples, times and locations where the soil samples are collected from the field 12. After processing the data, the data processor 26 may generate a map using the data to indicate the soil conditions of the field 12. The data processor 26 may be a central processing unit (CPU), a memory storage, a network, or the like. The data processor 26 may process the data using computational models, including, but not limited to, artificial intelligence (AI) techniques or other training techniques. The training techniques may further include graphics processing unit (GPU) parallelization, neural networks, or the like.

In some embodiments, the map may be generated using different colors to show the soil conditions of the soil in the field 12. For example, the map may use a dark color (e.g. dark blue) to indicate regions of the soil in the field 12 that are in healthy soil conditions. The healthy soil conditions mean that the soil in those regions (e.g. dark-colored regions) may include sufficient soil nutrient contents, including water and fertilizers, and may have an optimal pH environment for plant or crop growth. Additionally, the map may use a light color (e.g. light yellow) to indicate regions of the soil in the field 12 that are in less healthy soil conditions. The less healthy soil conditions signifies that the soil in those regions (e.g. light-colored) may lack of certain nutrient contents, such as water or fertilizers, and may not have a balance of the acidity and alkalinity of the soil (i.e. not having an optimal pH environment for plant or crop growth). In response, farmers may accordingly apply nutrients (e.g. water and/or fertilizers) to the soil in those regions to improve the soil conditions.

In some other embodiments, the map may be generated using a gradient of color to indicate the soil conditions of soil in the field 12. For example, the map may use a darker color (e.g. dark blue) to indicate regions of the soil having healthy soil conditions, and use a lighter color (e.g. light blue) to indicate regions of the soil having less healthy soil conditions.

Figure 2B:
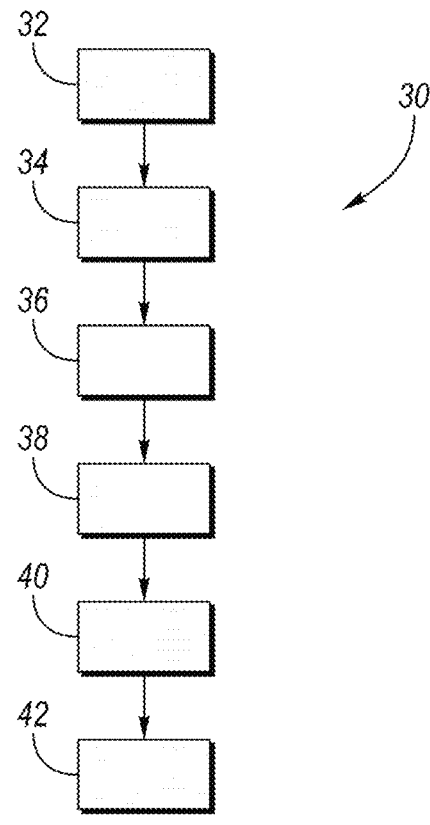
FIG. 2B depicts a flow chart illustrating a method of detecting soil conditions of the soil in a field (e.g. the field of FIG. 1) using the soil sampler described in FIG. 2A.

FIG. 2B depicts a flow chart illustrating a method of detecting soil conditions of the soil in a field (e.g. the field 12 of FIG. 1) using the soil sampler 14 described in FIG. 2A. The method 30 may include collecting soil samples from the field 12, step 32. The method 30 may further include preprocessing the soil samples, step 34. The method 30 may also include sensing at least one analyte in the soil samples, step 36. The method 30 may further include calculating a concentration of the at least one analyte in the soil samples, step 38. The method 30 may also include disposing the soil samples, step 40. The method 30 may further include generating a map indicating the soil conditions of the field 12 based on the concentration of the at least one analyte in the soil samples, step 42.

Figure 3:
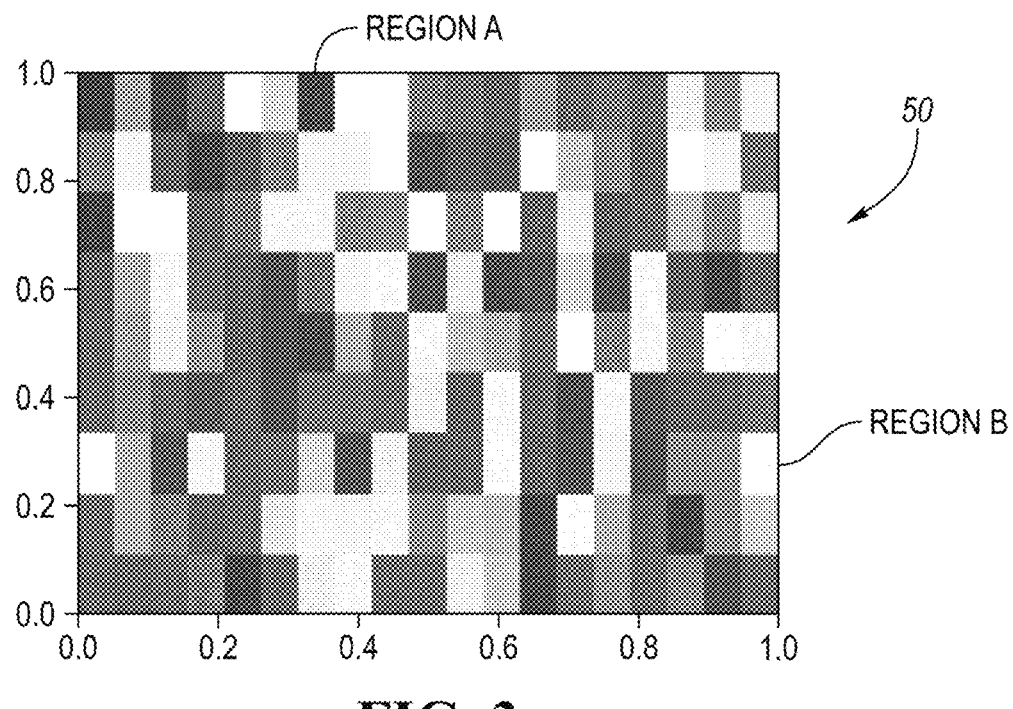
FIG. 3 depicts a representative image of a map generated by the soil sampler described in FIG. 2A.

FIG. 3 depicts a representative image of a map generated by the soil sampler 14 described in FIG. 2A. The image 50 may be a full map representing the soil conditions of the entire field (e.g. the field 12 of FIG. 1) or may be a portion of the full map that only shows the soil conditions of some regions of the entire field. The units for the x and y axis of the image 50 may be a fractional length along a width and a height of the field 12, respectively. Alternatively, the units may be any suitable metric units of length, such as kilometer (km) or meter (m). Although FIG. 3 shows that the image 50 is in a square shape, the shape of the image 50 may be rectangular, round, oval, irregular, or others. The shape of the image 50 may depend on the shape of the soil regions that are tested. Furthermore, although FIG. 3 shows evenly sampled grids of rectangles, the soil samples may be taken at arbitrary locations in the field that are not along the grids. In FIG. 3, the image 50 includes a gradient of color indicating the soil conditions of at least some regions of the soil in the entire field. Among these regions, region A is shown by a darker color, suggesting that region A may be in healthy soil conditions (e.g. with sufficient soil nutrient contents and an optimal pH). Region B, on the other hand, is displayed using a lighter color. This may be used to indicate that region B is in less healthy soil conditions (e.g. lack of certain nutrient contents and/or without an optimal pH), and that some actions may need to be taken to improve the soil conditions in region B.

Figure 4A:
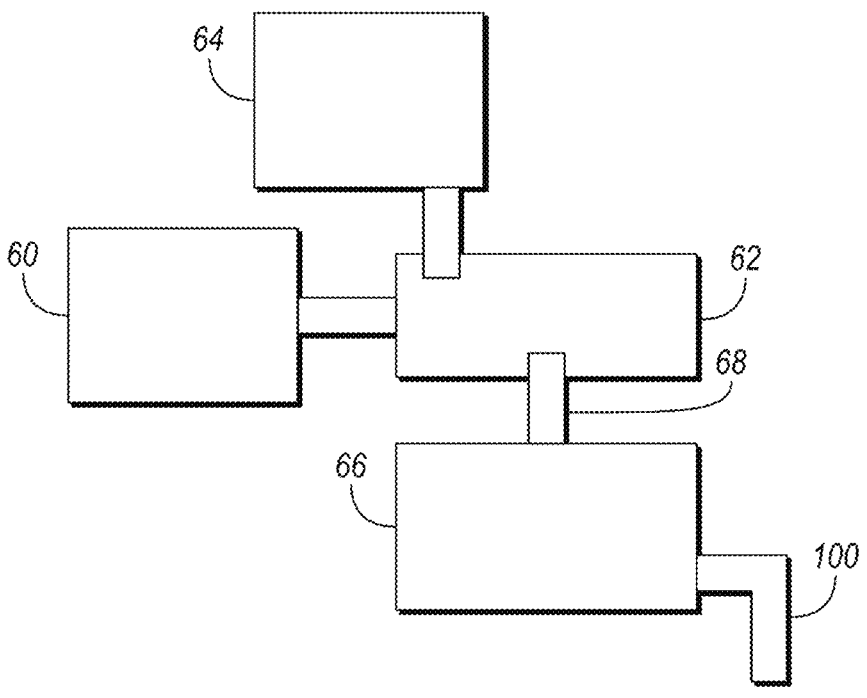
FIG. 4A depicts a schematic diagram of the soil sampler described in FIG. 2 according to a first embodiment of the present disclosure.

FIG. 4A depicts a schematic diagram of the soil sampler 14 described in FIG. 2 according to a first embodiment of the present disclosure. The soil sampler 14 may be disposed on a vehicle, for example, the vehicle 10 of FIG. 1. The soil sampler 14 may be disposed on a bottom side of the vehicle 10 facing a surface of a field (e.g. the field 12 of FIG. 1). The soil sampler 14 may be removably attached to the vehicle 10 or integrated with the vehicle 10. The soil sampler 14 may be configured to determine the soil conditions of the field as the vehicle 10 advances across the field. The soil sampler 14 may determine the soil conditions by detecting at least one analyte in the collected soil samples, and may further calculate a concentration of the at least one analyte in the soil samples. The at least one analyte may be ions. The at least one analyte may be N-containing analytes, P-containing analytes, K-containing analytes, Ca-containing analytes, Mg-containing analytes, S-containing analytes, Al-containing analytes, Ag-containing analytes, Pb-containing analytes, or a combination thereof. The N-containing analytes may be $NO_3^-$ or $NH_4^+$ ions.

As shown in FIG. 4A, the soil sampler 14 may include a collector 60 configured to collect soil samples from the field as the vehicle 10 advances across the field. The collector 60 may be a soil probe, which, upon a force is applied thereto, may extend a depth into the field to obtain a soil sample. In some embodiments, the soil sample may include a soil amount of 1 to 10 g.

Referring to FIG. 4A, the soil sampler 14 may further include a preprocessor 62 connected to the collector 60. The preprocessor 62 may receive the soil sample from the collector 60. The preprocessor 62 may initially obtain a baseline measurement without the presence of the soil sample. In FIG. 4A, the soil sampler 14 may further include a tank 64 connected to the preprocessor 62. The tank 64 may include a liquid. The liquid may be water. The water may be deionized water, tap water, or water with known ion contents. To preprocess the soil sample, the tank 64 may be configured to supply the liquid to the preprocessor 62, where the soil sample may be diluted with the liquid. A ratio of the soil amount in the soil sample to the liquid is at least 0.1.

As shown in FIG. 4A, the soil sampler 14 may also include a sensor 66 connected to the preprocessor 62. The sensor 66 may receive a preprocessed soil sample (i.e. diluted soil sample) from the preprocessor 62. In some embodiments, microfluidic channels 68 may be used to connect the preprocessor 62 and the sensor 66. The microfluidic channels 68 may have a width of less than 1 millimeter (mm). Some of the advantages of using microfluidic channels with a width of less than 1 mm are energy conservation, optimal fluid-solid separation and great flow control. The microfluidic channels 68 may also have a width of more than 1 mm to avoid clogging.

Figure 4B:
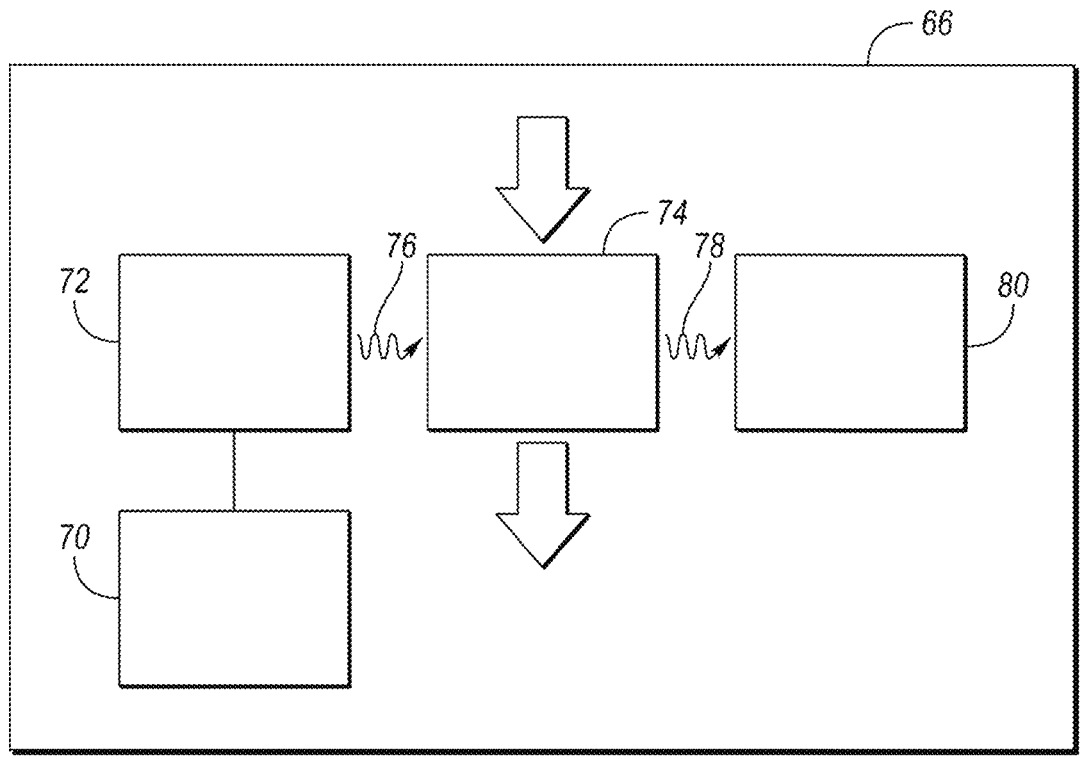
FIG. 4B depicts a schematic diagram of the sensor of FIG. 4A.

FIG. 4B depicts a schematic diagram of the sensor 66 of FIG. 4A. As shown in FIG. 4B, the sensor 66 may include a power source 70 and an optical source 72 powered by the power source 70. The sensor 66 may further include at least one chemosensor positioned in a sensing chamber 74 of the sensor 66. The preprocessed soil sample may pass through the sensing chamber 74, indicated by the arrows in FIG. 4B. The at least one chemosensor may be embedded in or attached to a sensor film. The at least one chemosensor may be configured to capture (e.g. bind to) at least one analyte in the soil sample. The optical source 72 may emit light 76 to the at least one chemosensor. Upon capturing the at least one analyte, the at least one chemosensor may generate a signal 78, such as by causing or quenching fluorescence. The sensor 66 may further include a detector 80 configured to receive the signal and to calculate a concentration of the at least one analyte in the soil sample based on the signal. The detector 80 may be a photodetector, such as a photodiode or a photoresistor. Apart from chemosensors, the sensor 66 may also incorporate other types of sensors for analyte detection.

Figure 4C:
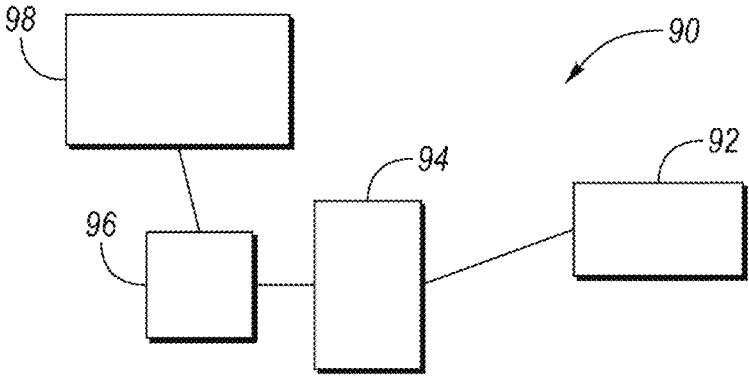
FIG. 4C depicts a schematic diagram of a chemosensor configured to be used in the sensor described in FIG. 4B.

FIG. 4C depicts a schematic diagram of a chemosensor configured to be used in the sensor 66 described in FIG. 4B. As shown in FIG. 4C, the chemosensor 90 is a receptor/spacer/fluorophore-type sensor. Specifically, the chemosensor 90 may be linked to a tethering matrix via an anchor 92 thereof. The tethering matrix may include, but not limited to, cellulose microparticles, cellulose films, polymethyl methacrylate (PMMA), polystyrene (PS) microparticles, polyethylene terephthalate (PET) layers, or silicone. The tethering matrix may have a size in a range of 1 to 100 μm and may be embedded within hydrogels. The hydrogels may be, but not limited to, polyurethane or poly(2-hydroxyethyl methacrylate) (Poly-HEMA). In addition, the tethering matrix and the hydrogels may be supported by a polymer support. The polymer support may be, but not limited to, PET. The chemosensor 90 may also include a fluorophore 94 bound to the anchor 92, and a space 96 bound to the fluorophore 94. The fluorophore 94 may be, but not limited to, anthracene, benzene, carbazole, diphenylfurane, naphthalene, 1,8-naphthalimide, N,N,N',N'-tetramethylbenzidine, porphyrin, or pyrene. The spacer 96 may be, but not limited to, methylamine and ethylamine. Furthermore, the chemosensor 90 includes a receptor 98 bound to the spacer 96, where the receptor 98 may coordinate to at least one analyte in the soil sample for analyte detection.

Continuing referring to FIG. 4A, the soil sampler 14 may also include a disposer 100 connected to the sensor 66. The disposer 100 may be configured to dispose the soil sample back to the field after sensing. Alternatively, the soil sampler 14 may optionally include a waste reservoir, and the disposer may be configured to dispose the soil sample to the waste reservoir after sensing. In some embodiments, the disposer 100 may further include a cleaning cycle configured to rinse the soil sampler with clean water after sensing.

Figure 4D:
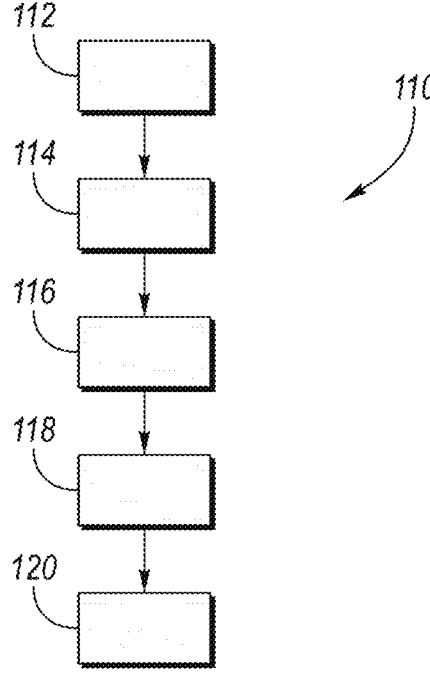
FIG. 4D depicts a flow chart illustrating a method of detecting soil conditions of the soil in a field (e.g. a ground or soil) using the soil sampler described in FIG. 4A.

FIG. 4D depicts a flow chart illustrating a method of detecting soil conditions of the soil in a field (e.g. a ground or soil) using the soil sampler 14 described in FIG. 4A. Referring to FIG. 4D, the method 110 may include collecting a soil sample from the field as the vehicle advances across the field, step 112. The method 110 may further include diluting the soil sample with a liquid to obtain a preprocessed soil sample (e.g. a diluted soil sample), step 114. The liquid may be water. The method 110 may also include capturing (e.g. binding to) at least one analyte in the preprocessed soil sample using at least one chemosensor and generating a signal (e.g. fluorescence) in response to capturing the at least one analyte, step 116. The method 110 may further include calculating a concentration of the at least one analyte in the soil sample based on the signal, step 118. The method may also include disposing the soil sample, for example, back to the field, step 120.

FIG. 5A depicts a schematic diagram of the soil sampler 14 described in FIG. 2 according to a second embodiment of the present disclosure. The soil sampler 14 may be disposed on a vehicle, for example, the vehicle 10 of FIG. 1. The soil sampler 14 may be disposed on a bottom side of the vehicle 10 facing a surface of a field (e.g. the field 12 of FIG. 1). The soil sampler 14 may be removably attached to the vehicle 10 or integrated with the vehicle 10. The soil sampler 14 may be configured to determine the soil conditions of the field as the vehicle 10 advances across the field. The soil sampler 14 may determine the soil conditions by detecting at least one analyte in the collected soil samples, and may further calculate a concentration of the at least one analyte in the soil samples. The at least one analyte may be ions. The at least one analyte may be N-containing analytes, P-containing analytes, K-containing analytes, Ca-containing analytes, Mg-containing analytes, S-containing analytes, Al-containing analytes, Ag-containing analytes, Pb-containing analytes, or a combination thereof. The N-containing analytes may be $NO_3^-$ or $NH_4^+$ ions.

As shown in FIG. 5A, the soil sampler 14 may include a collector 140 configured to collect soil samples from the field as the vehicle 10 advances across the field. The collector 140 may be a soil probe, which, upon a force is applied thereto, may extend a depth into the field to obtain a soil sample. In some embodiments, the soil sample may include a soil amount of 1 to 10 g.

Referring to FIG. 5A, the soil sampler 14 may further include a preprocessor 142 connected to the collector 140. The preprocessor 142 may receive the soil sample from the collector 140. The preprocessor 142 may initially obtain a baseline measurement without the presence of the soil sample. In FIG. 5A, the soil sampler 14 may further include a first tank 144 connected to the preprocessor 142. The first tank 144 may include a liquid. The liquid may be water. The water may be deionized water, tap water, or water with known ion contents. The soil sampler 14 may also include a second tank 146 connected to the preprocessor 142. The second tank 146 may include a chemical reagent. The chemical reagent may be a color reagent, such as sodium acetate. To preprocess the soil sample, the first tank 144 may be configured to supply the liquid to the preprocessor 142, and the second tank 146 may be configured to supply the chemical reagent to the preprocessor 142, where the soil sample may be diluted with the liquid in the presence of the chemical reagent. While in the preprocessor 142, the chemical reagent may react with at least one analyte in the diluted soil sample, resulting in a color change of the diluted soil sample with a color intensity. The color intensity may depend on the concentration of the at least one analyte in the diluted soil sample, which can be measured photometrically.

As shown in FIG. 5A, the soil sampler 14 may also include a sensor 148 connected to the preprocessor 142. The sensor 148 may receive a preprocessed soil sample (i.e. the diluted soil sample) from the preprocessor 142. In some embodiments, microfluidic channels 150 may be used to connect the preprocessor 142 and the sensor 148. The microfluidic channels 150 may have a width of less than 1 millimeter (mm). Some of the advantages of using microfluidic channels with a width of less than 1 mm are energy conservation, optimal fluid-solid separation and great flow control. The microfluidic channels 150 may also have a width of more than 1 mm to avoid clogging.

FIG. 5B depicts a schematic diagram of the sensor 148 in FIG. 5A. As shown in FIG. 5B, the sensor 148 may include a power source 152 and an optical source 154 powered by the power source 152. The sensor 148 may further include a sensing chamber 156 through which the preprocessed soil sample (e.g. the colored soil sample) passes, indicated by the arrows in FIG. 5B. The optical source 154 may emit light 158 to the preprocessed soil sample when it passes through the sensing chamber 156. The sensor may also include an optical detector 160 with optical color filters configured to detect at least one analyte in the soil sample based on an emitted color 162 (i.e. the color change) of the soil sample and to calculate a concentration of the at least one analyte in the soil sample by colorimetric analysis, i.e. by measuring the color intensity of the soil sample. The optical detector 160 may be a camera or a photodiode.

Continuing referring to FIG. 5A, the soil sampler may include a disposer 164 connected to the sensor 148. The disposer 164 may be configured to dispose the soil sample to a waste reservoir 166 of the soil sampler 14. In some embodiments, the disposer 164 may also include a cleaning cycle configured to rinse the soil sampler 14 with clean water after sensing.

FIG. 5C depicts a flow chart illustrating a method of detecting soil conditions of the soil in a field (e.g. a ground or soil) using the soil sampler described in FIG. 5A. Referring to FIG. 5C, the method 180 may include collecting a soil sample from the field as the vehicle advances across the field, step 182. The method 180 may further include diluting the soil sample with a liquid, followed by adding a chemical reagent to the diluted soil sample to obtain a preprocessed soil sample, step 184. The liquid may be water. The chemical reagent may be a color reagent, such as sodium acetate. The preprocessed soil sample may have a color with a color intensity. The method 180 may also include measuring the color intensity of the soil sample using an optical detector with optical color filters, step 186. The method 180 may further include determining a concentration of at least one analyte in the soil sample based on the color intensity of the soil sample, step 188. The optical detector may be a camera or a photodiode. The method 180 may also include disposing the soil sample to a waste reservoir, step 190.

Figure 6A:
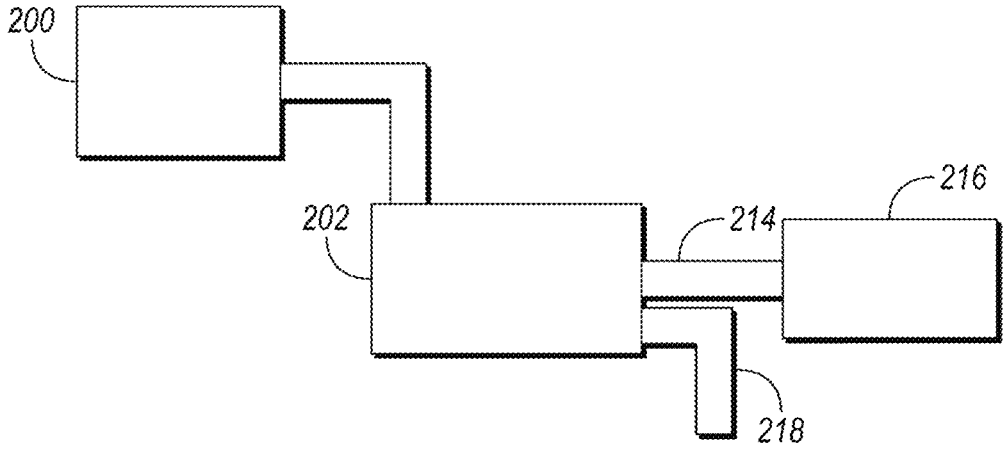
FIG. 6A depicts a schematic diagram of the soil sampler described in FIG. 2 according to a third embodiment of the present disclosure.

FIG. 6A depicts a schematic diagram of the soil sampler 14 described in FIG. 2 according to a third embodiment of the present disclosure. The soil sampler 14 may be disposed on a vehicle, for example, the vehicle 10 of FIG. 1. The soil sampler 14 may be disposed on a bottom side of the vehicle 10 facing a surface of a field (e.g. the field 12 of FIG. 1). The soil sampler 14 may be removably attached to the vehicle 10 or integrated with the vehicle 10. The soil sampler 14 may be configured to determine the soil conditions of the field as the vehicle 10 advances across the field. The soil sampler 14 may determine the soil conditions by detecting at least one analyte in the collected soil samples, and may further calculate a concentration of the at least one analyte in the soil samples. The at least one analyte may be ions. The at least one analyte may be N-containing analytes, P-containing analytes, K-containing analytes, Ca-containing analytes, Mg-containing analytes, S-containing analytes, Al-containing analytes, Ag-containing analytes, Pb-containing analytes, or a combination thereof. The N-containing analytes may be $NO_3^-$ or $NH_4^+$ ions.

As shown in FIG. 6A, the soil sampler 14 may include a collector 200 configured to collect soil samples from the field as the vehicle 10 advances across the field. The collector 200 may be a soil probe, which, upon a force is applied thereto, may extend a depth into the field to obtain a soil sample. In some embodiments, the soil sample may include a soil amount of 1 to 10 g.

Figure 6B:
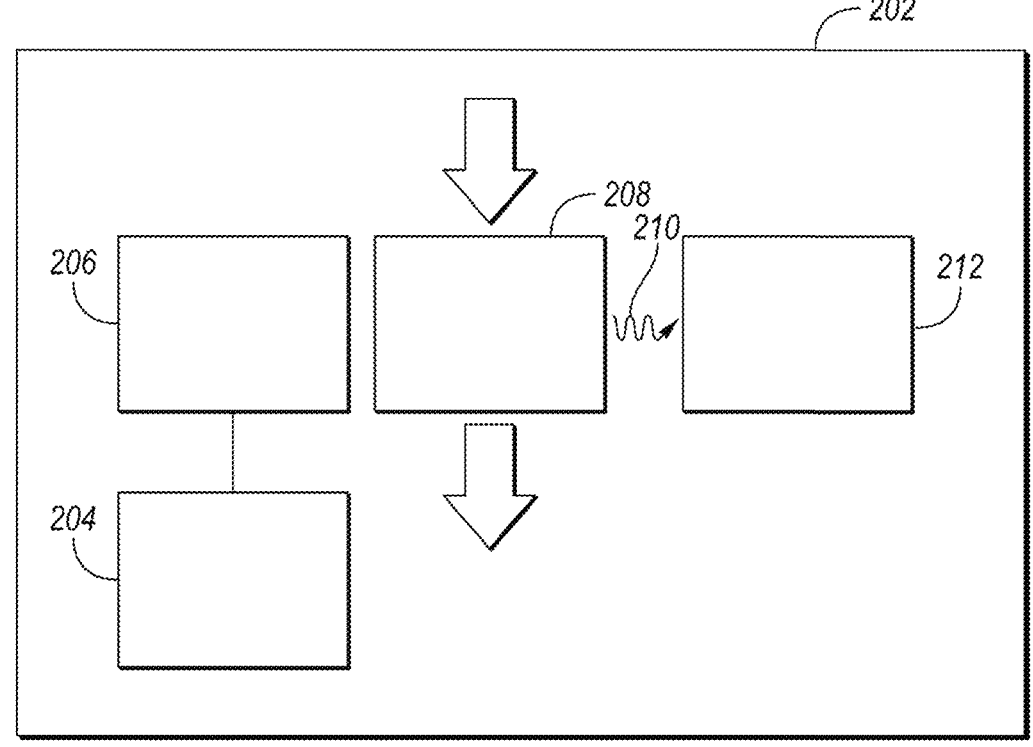
FIG. 6B depicts a schematic diagram of the sensor in FIG. 6A.

As shown in FIG. 6A, the soil sampler 14 may also include a sensor 202 connected to the collector 200. The sensor 202 may receive the soil sample from the collector 200. FIG. 6B depicts a schematic diagram of the sensor 202 in FIG. 6A. As shown in FIG. 6B, the sensor 202 may include a power source 204 and a heat source 206 powered by the power source 204. The sensor 202 may further include a sensing chamber 208 through which the soil sample passes, indicated by the arrows in FIG. 6B. The heat source 206 may be configured to emit heat to the soil sample to vaporize the soil sample, thereby generating light 210 with an optical frequency (e.g. an absorption or emission spectrum). The sensor 202 may further include an optical spectrum sensor 212 configured to receive and measure the optical frequency and to calculate a concentration of at least one analyte in the soil sample based on the optical frequency.

Continuing referring to FIG. 6A, the soil sampler 14 may include a first disposer 214 connected to the sensor 202. The first disposer 214 may be configured to dispose the soil sample to a waste reservoir 216 of the soil sampler 14 after sensing. The soil sampler 14 may also include a second disposer 218 connected to the sensor 202. The second disposer 218 may be configured to dispose the soil sample back to the field after sensing. In some embodiments, the first or second disposer, 214 or 218, may also include a cleaning cycle configured to rinse the soil sampler with clean water after sensing.

Figure 6C:
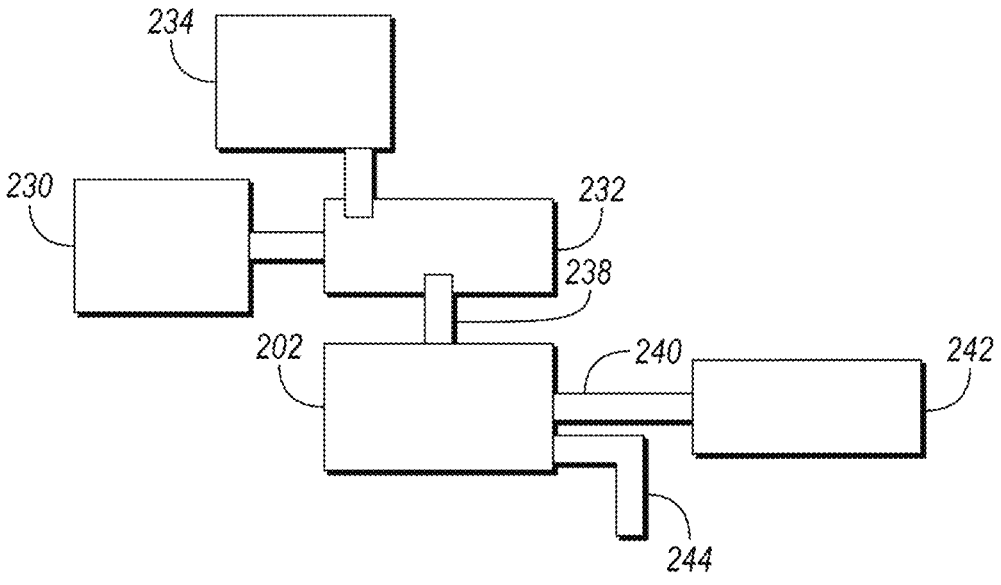
FIG. 6C depicts a schematic diagram of the soil sampler described in FIG. 2 according to a fourth embodiment of the present disclosure.

FIG. 6C depicts a schematic diagram of the soil sampler 14 described in FIG. 2 according to a fourth embodiment of the present disclosure. The soil sampler 14 may be disposed on a vehicle, for example, the vehicle 10 of FIG. 1. The soil sampler 14 may be disposed on a bottom side of the vehicle 10 facing a surface of a field (e.g. the field 12 of FIG. 1). The soil sampler 14 may be removably attached to the vehicle 10 or integrated with the vehicle 10. The soil sampler 14 may be configured to determine the soil conditions of the field as the vehicle 10 advances across the field. The soil sampler 14 may determine the soil conditions by detecting at least one analyte in the collected soil samples, and may further calculate a concentration of the at least one analyte in the soil samples. The at least one analyte may be ions. The at least one analyte may be N-containing analytes, P-containing analytes, K-containing analytes, Ca-containing analytes, Mg-containing analytes, S-containing analytes, Al-containing analytes, Ag-containing analytes, Pb-containing analytes, or a combination thereof. The N-containing analytes may be $NO_3^-$ or $NH_4^+$ ions.

As shown in FIG. 6C, the soil sampler 14 may include a collector 230 configured to collect soil samples from the field as the vehicle 10 advances across the field. The collector 230 may be a soil probe, which, upon a force is applied thereto, may extend a depth into the field to obtain a soil sample. In some embodiments, the soil sample may include a soil amount of 1 to 10 g.

Referring to FIG. 6C, the soil sampler 14 may further include a preprocessor 232 connected to the collector 230. The preprocessor 232 may receive the soil sample from the collector 230. The preprocessor 232 may initially obtain a baseline measurement without the presence of the soil sample. In FIG. 6C, the soil sampler 14 may further include a tank 234 connected to the preprocessor 232. The tank 234 may include a liquid. The liquid may be water. The water may be deionized water, tap water, or water with known ion contents. To preprocess the soil sample, the tank 234 may supply the liquid to the preprocessor 232, where the soil sample may be diluted with the liquid. A ratio of the soil amount in the soil sample to the liquid is at least 0.1. In some embodiments, the preprocessor 232 may optionally centrifuge and/or filter the diluted soil sample to remove some particles in the soil sample. Examples of the particles may include rocks, oils, glass, plastics, or the like.

As shown in FIG. 6C, the soil sampler 14 may also include a sensor 202 connected to the preprocessor 232. The sensor 202 may be the sensor described in FIG. 6B. The sensor 202 may receive a preprocessed soil sample from the preprocessor 232. In some embodiments, microfluidic channels 238 may be used to connect the preprocessor 232 and the sensor 202. The microfluidic channels 238 may have a width of less than 1 millimeter (mm). Some of the advantages of using microfluidic channels with a width of less than 1 mm are energy conservation, optimal fluid-solid separation and great flow control. The microfluidic channels 238 may also have a width of more than 1 mm to avoid clogging.

Continuing referring to FIG. 6C, the soil sampler 14 may include a first disposer 240 connected to the sensor 202. The first disposer 240 may be configured to dispose the soil sample to a waste reservoir 242 of the soil sampler 14 after sensing. The soil sampler 14 may also include a second disposer 244 connected to the sensor 202. The second disposer 244 may be configured to dispose the soil sample back to the field after sensing. In some embodiments, the first or second disposer, 240 or 244, may also include a cleaning cycle configured to rinse the soil sampler with clean water after sensing.

Figure 6D:
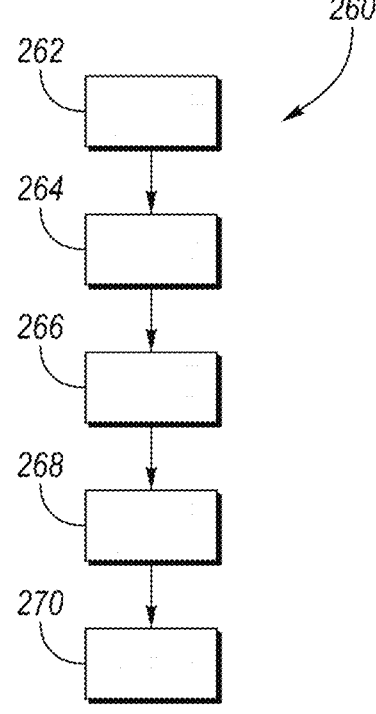
FIG. 6D depicts a flow chart illustrating a method of detecting soil conditions of the soil in a field (e.g. a ground or soil) using the soil sampler described in FIG. 6A.

FIG. 6D depicts a flow chart illustrating a method of detecting soil conditions of the soil in a field (e.g. a ground or soil) using the soil sampler 14 described in FIG. 6A. Referring to FIG. 6D, the method 260 may include collecting a soil sample from the field as the vehicle advances across the field, step 262. The method 260 may further include vaporizing the soil sample, thereby generating light with an optical frequency (e.g. an absorption or emission spectrum), step 264. The method 260 may also include measuring the optical frequency using an optical spectrum sensor, step 266. The method 260 may further include calculating a concentration of at least one analyte in the soil sample based on the optical frequency, step 268. The method 260 may further include disposing the soil sample, for example, back to the field or to a waste reservoir, step 270.

FIG. 7A depicts a schematic diagram of the soil sampler 14 described in FIG. 2 according to a fifth embodiment of the present disclosure. The soil sampler 14 may be disposed on a vehicle, for example, the vehicle 10 of FIG. 1. The soil sampler 14 may be disposed on a bottom side of the vehicle 10 facing a surface of a field (e.g. the field 12 of FIG. 1). The soil sampler 14 may be removably attached to the vehicle 10 or integrated with the vehicle 10. The soil sampler 14 may be configured to determine the soil conditions of the field as the vehicle 10 advances across the field. The soil sampler 14 may determine the soil conditions by detecting at least one analyte in the collected soil samples, and may further calculate a concentration of the at least one analyte in the soil samples. The at least one analyte may be ions. The at least one analyte may be N-containing analytes, P-containing analytes, K-containing analytes, Ca-containing analytes, Mg-containing analytes, S-containing analytes, Al-containing analytes, Ag-containing analytes, Pb-containing analytes, or a combination thereof. The N-containing analytes may be $NO_3^-$ or $NH_4^+$ ions.

As shown in FIG. 7A, the soil sampler 14 may include a collector 290 configured to collect soil samples from the field as the vehicle 10 advances across the field. The collector 290 may be a soil probe, which, upon a force is applied thereto, may extend a depth into the field to obtain a soil sample. In some embodiments, the soil sample may include a soil amount of 1 to 10 g.

Referring to FIG. 7A, the soil sampler 14 may further include a preprocessor 292 connected to the collector 290. The preprocessor 292 may receive the soil sample from the collector 290. The preprocessor 292 may initially obtain a baseline measurement without the presence of the soil sample. In FIG. 7A, the soil sampler 14 may further include a tank 294 connected to the preprocessor 292. The tank 294 may include a liquid. The liquid may be water. The water may be deionized water, tap water, or water with known ion contents. To preprocess the soil sample, the tank 294 may supply the liquid to the preprocessor 292, where the soil sample may be diluted with the liquid A ratio of the soil amount in the soil sample to the liquid is at least 0.1.

As shown in FIG. 7A, the soil sampler 14 may also include a sensor 296 connected to the preprocessor 292. The sensor 296 may receive a preprocessed soil sample (i.e. the diluted soil sample) from the preprocessor 292. In some embodiments, microfluidic channels 298 may be used to connect the preprocessor 292 and the sensor 296. The microfluidic channels 298 may have a width of less than 1 millimeter (mm). Some of the advantages of using microfluidic channels with a width of less than 1 mm are energy conservation, optimal fluid-solid separation and great flow control. The microfluidic channels 298 may also have a width of more than 1 mm to avoid clogging.

FIG. 7B depicts a schematic diagram of the sensor 296 in FIG. 7A. As shown in FIG. 7B, the sensor 296 may include a first electrode 300 and a second electrode 302 electrically coupled to the first electrode 300. The first electrode 300 may be a reference electrode. The sensor 296 may further include a sensing chamber 304 through which a preprocessed soil sample (e.g. the diluted soil sample) passes, indicated by the arrows in FIG. 7B.

In some embodiments, the second electrode 302 may be an ion-selective electrode (ISE). The ISE may be a metal oxide. The ISE may also be an electrode covered with an ion-selective membrane, such as a polymer. The ISE may be configured to bind to at least one analyte in the soil sample as the soil sample passes through the sensing chamber 304. Upon binding to the at least one analyte, a change of an electrical potential of the ISE may be generated. The sensor 296 may further include a detector 306 electrically coupled to the ISE and the first electrode 300. The detector 306 may be configured to detect the change of the electrical potential and to calculate a concentration of the at least one analyte in the soil sample based on the change of the electrical potential.

In some other embodiments, the second electrode 302 may be an intercalation electrode. The intercalation electrode may be made of a Prussian Blue (PB)-type compound or metal hexacyanoferrate (MHCFe), where M may be nickel (Ni), copper (Cu), cobalt (Co), or manganese (Mn). For example, NiHCFe may operate within 0 to 0.8 V vs SHE (i.e. standard hydrogen electrode) to detect cations such as sodium ions ($Na^+$). The intercalation electrode may also be a Prussian Blue Analog (PBA) consisting of one or more transition metals, carbon-nitrogen pairs, and containing a crystal structure similar to a PB-type compound or MHCFe, as disclosed herein. The intercalation electrode may be configured to intercalate at least one analyte in the soil sample at certain potentials as the soil sample passes through the sensing chamber 304. Upon intercalating the at least one analyte, a change of an open-circuit voltage of the intercalation electrode may be generated. The sensor 296 may further include a detector 306 electrically coupled to the intercalation electrode and the reference electrode. The detector 306 may be configured to detect the change of the open-circuit voltage and to calculate a concentration of the at least one analyte in the soil sample based on the change of the open-circuit voltage. An external power may be applied to the intercalation electrode to deintercalate the at least one analyte if needed.

Continuing referring to FIG. 7A, the soil sampler 14 may include a first disposer 308 connected to the sensor 296. The first disposer 308 may be configured to dispose the soil sample to a waste reservoir 310 of the soil sampler 14 after sensing. The soil sampler 14 may also include a second disposer 312 connected to the sensor 296. The second disposer 312 may be configured to dispose the soil sample back to the field after sensing. In some embodiments, the first or second disposer, 308 or 312, may also include a cleaning cycle configured to rinse the soil sampler with clean water after sensing.

FIG. 7C depicts a flow chart illustrating a method of detecting soil conditions of the soil in a field (e.g. a ground or soil) using the soil sampler 14 described in FIG. 7A. Referring to FIG. 7C, the method 330 may include collecting a soil sample from the field as the vehicle advances across the field, step 332. The method 330 may further include diluting the soil sample with a liquid, step 334. The liquid may be water. The method 330 may also include binding to or intercalate at least one analyte in the soil sample using an electrode, which, upon binding or intercalation, generates a change of an electrical potential or a change of an open-circuit voltage of the electrode, step 336. The electrode may be an ion-selective electrode (ISE) or an intercalation electrode, respectively. The method 330 may further include detecting the change of the electrical potential or the change of the open-circuit voltage, step 338. The method 330 may also include calculating a concentration of the at least one analyte in the soil sample based on the change of the electrical potential or the change of the open-circuit voltage, step 340. The method 330 may also include disposing the soil sample, step 342.

The preprocessors and processors disclosed herein may be part of, or include, processor hardware (shared, dedicated, or group) that executes code and memory hardware (shared, dedicated, or group) that stores code executed by the preprocessor or processor hardware. The code is configured to provide the features of the preprocessors or processors described herein. In one example, the processor or preprocessor may refer to a larger controller that includes a processor, memory, and non-volatile storage. The processor or preprocessor may include one or more soil samplers selected from microprocessors, micro-controllers, digital signal processors, microcomputers, central processing units, field programmable gate arrays, programmable logic soil samplers, state machines, logic circuits, analog circuits, digital circuits, or any other soil samplers that manipulate signals (analog or digital) based on computer-executable instructions residing in memory. The memory may include a single memory soil sampler or a plurality of memory soil samplers including, but not limited to, random access memory ("RAM"), volatile memory, non-volatile memory, static random-access memory ("SRAM"), dynamic random-access memory ("DRAM"), flash memory, cache memory, or any other soil sampler capable of storing information. The non-volatile storage may include one or more persistent data storage soil samplers such as a hard drive, optical drive, tape drive, non-volatile solid-state soil sampler, or any other soil sampler capable of persistently storing information. The processor or preprocessor may be configured to read into memory and execute computer-executable instructions embodying one or more software programs residing in the non-volatile storage. Programs residing in the non-volatile storage may include or be part of an operating system or an application, and may be compiled or interpreted from computer programs created using a variety of programming languages and/or technologies, including, without limitation, and either alone or in combination, Java, C, C++, C#, Objective C, Fortran, Pascal, Java Script, Python, Perl, and PL/SQL. The computer-executable instructions of the programs may be configured, upon execution by the processor, to determine a concentration of at least one analyte in a soil sample, and a time and a location where the soil sample is collected from a field, and generate a map using the data to indicate soil conditions of the location in the field, for example.

Implementations of the subject matter and the operations described in this specification can be implemented in digital electronic circuitry, or in computer software embodied on a tangible medium, firmware, or hardware, including the structures disclosed in this specification and their structural equivalents, or in combinations of one or more of them. Implementations of the subject matter described in this specification can be implemented as one or more computer programs embodied on a tangible medium, i.e., one or more modules of computer program instructions, encoded on one or more computer storage media for execution by, or to control the operation of, a data processing apparatus. A computer storage medium can be, or be included in, a computer-readable storage soil sampler, a computer-readable storage substrate, a random or serial access memory array or soil sampler, or a combination of one or more of them. The computer storage medium can also be, or be included in, one or more separate components or media (e.g., multiple CDs, disks, or other storage soil samplers). The computer storage medium may be tangible and non-transitory.

A computer program (also known as a program, software, software application, script, or code) can be written in any form of programming language, including compiled languages, interpreted languages, declarative languages, and procedural languages, and the computer program can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, libraries, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., a field programmable gate array ("FPGA") or an application specific integrated circuit ("ASIC"). Such a special purpose circuit may be referred to as a computer processor even if it is not a general-purpose processor.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A soil sampler attachable to a vehicle for monitoring soil conditions in real time as the vehicle advances across a field, the soil sampler comprising:

a collector configured to collect a soil sample from the field as the vehicle advances across the field;

a preprocessor connected to the collector and configured to receive the soil sample from the collector and dilute the soil sample as the vehicle advances across the field;

a sensor connected to the preprocessor and configured to determine a concentration of at least one analyte in the diluted soil sample as the vehicle advances across the field; and a disposer connected to the sensor and configured to dispose the diluted soil sample; and one or more processors programmed to:

dilute the soil sample via the preprocessor as the vehicle advances across the field, via the sensor, determine the concentration of the at least one analyte in the diluted soil sample as the vehicle advances across the field, and cause the disposer to dispose the diluted soil sample as the vehicle advances across the field based on the determined concentration of the at least one analyte in the soil sample.

2. The soil sampler of claim 1, further comprising a tracker connected to the one or more processors and configured to record a time and a location where the soil sample is collected from the field, wherein the tracker is a global positioning system (GPS) tracker, a Bluetooth tracker, a near-field communication (NFC) tracker, or a Wi-Fi tracker.

3. The soil sampler of claim 2, wherein the one or more processors is further programmed to:

generate a map based on the determined concentration of the at least one analyte in the diluted soil sample and the recorded time and location where the diluted soil sample is collected from the field to indicate soil conditions of the location in the field.

4. The soil sampler of claim 1, further comprising a first tank connected to the preprocessor, wherein the first tank includes a liquid and is configured to supply the liquid to the preprocessor to dilute the soil sample in the preprocessor.

5. The soil sampler of claim 4, wherein the liquid is water.

6. The soil sampler of claim 4, further comprising a second tank connected to the preprocessor, wherein the second tank includes a color reagent and is configured to supply the color reagent to the preprocessor, wherein when the color reagent reacts with at least one analyte in the diluted soil sample, a color change of the diluted soil sample occurs with a color intensity.

7. The soil sampler of claim 6, wherein the color reagent is sodium acetate.

8. The soil sampler of claim 6, wherein the sensor further includes:

a power source;

an optical source powered by the power source and configured to emit light to the diluted soil sample; and an optical detector with optical color filters configured to detect the at least one analyte in the diluted soil sample based on the color change of the diluted soil sample and to calculate a concentration of the at least one analyte in the diluted soil sample based on the color intensity of the diluted soil sample.

9. The soil sampler of claim 1, wherein the sensor further includes:

at least one chemosensor configured to capture at least one analyte in the diluted soil sample and to generate a signal in response to capturing the at least one analyte; and a detector configured to receive the signal and to calculate a concentration of the at least one analyte in the soil sample based on the signal.

10. The soil sampler of claim 9, wherein the at least one chemosensor includes a receptor configured to capture the at least one analyte in the diluted soil sample, and further including a spacer bound to the receptor, a fluorophore bound to the spacer, and an anchor bound to the fluorophore.

11. The soil sampler of claim 10, wherein the fluorophore is selected from the group consisting of anthracene, benzene, carbazole, diphenylfurane, naphthalene, 1,8-naphthalimide, N,N,N',N'-tetramethylbenzidine, porphyrin, and pyrene.

12. The soil sampler of claim 1, wherein the sensor further includes:

a first electrode;

a second electrode electrically coupled to the first electrode, wherein the second electrode is an ion-selective electrode configured to bind to the at least one analyte in the diluted soil sample and to generate a change of an electrical potential in response to binding to the at least one analyte; and a detector electrically coupled to the first and second electrodes and to detect the change of the electrical potential and to calculate a concentration of the at least one analyte in diluted the soil sample based on the change of the electrical potential.

13. The soil sampler of claim 12, wherein the ion-selective electrode is a metal oxide or an electrode covered with an ion-selective membrane.

14. The soil sampler of claim 1, wherein the sensor further includes:

a first electrode;

a second electrode electrically coupled to the first electrode, wherein the second electrode is an intercalation electrode configured to intercalate the at least one analyte in the diluted soil sample and to generate a change of an open-circuit voltage in response to intercalating the at least one analyte; and a detector electrically coupled to the first and second electrodes and to detect the change of the open-circuit voltage and to calculate a concentration of the at least one analyte in the diluted soil sample based on the change of the open-circuit voltage.

15. The soil sampler of claim 14, wherein the intercalation electrode is made of a Prussian Blue (PB)-type compound or metal hexacyanoferrate (MHCFe), where M is nickel (Ni), copper (Cu), cobalt (Co), or manganese (Mn).

16. The soil sampler of claim 1, wherein the preprocessor and the sensor are connected using microfluidic channels.

17. The soil sampler of claim 1, wherein the at least one analyte is a nitrogen (N)-containing analyte, a phosphorus (P)-containing analyte, a potassium (K)-containing analyte, a calcium (Ca)-containing analyte, a magnesium (Mg)-containing analyte, a sulfur(S)-containing analyte, an aluminum (Al)-containing analyte, a silver (Ag)-containing analyte, a lead (Pb)-containing analyte, or a combination thereof.

18. The soil sampler of claim 1, wherein the at least one processor is programmed to cause the disposer to dispose of the diluted soil sample back onto field as the vehicle advances across the field based on the determined concentration of the at least one analyte in the soil sample.

19. The soil sampler of claim 1, further comprising a waste reservoir, wherein the at least one processor is programmed to cause the disposer to dispose of the diluted soil sample into the waste reservoir as the vehicle advances across the field based on the determined concentration of the at least one analyte in the soil sample.

* * * * *